(12) United States Patent
Berg

(10) Patent No.: US 8,452,396 B2
(45) Date of Patent: May 28, 2013

(54) SYNCHRONIZATION OF ELECTRICAL STIMULATION THERAPY TO TREAT CARDIAC ARRHYTHMIAS

(75) Inventor: Gary L. Berg, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 120 days.

(21) Appl. No.: 12/982,603

(22) Filed: Dec. 30, 2010

(65) Prior Publication Data

US 2012/0172942 A1 Jul. 5, 2012

(51) Int. Cl.
*A61N 1/00* (2006.01)

(52) U.S. Cl.
USPC ............................................................. 607/5

(58) Field of Classification Search
USPC .............................................. 607/5; 600/515
See application file for complete search history.

(56) References Cited

U.S. PATENT DOCUMENTS

| | | | | |
|---|---|---|---|---|
| 4,779,617 A * | 10/1988 | Whigham | | 607/9 |
| 5,179,945 A | 1/1993 | Van Hofwegen et al. | | |
| 5,188,105 A | 2/1993 | Keimel | | |
| 5,275,621 A | 1/1994 | Mehra | | |
| 5,279,291 A | 1/1994 | Adams et al. | | |
| 5,545,186 A | 8/1996 | Olson et al. | | |
| 5,584,864 A | 12/1996 | White | | |
| 5,755,736 A | 5/1998 | Gillberg et al. | | |
| 5,836,976 A | 11/1998 | Min et al. | | |
| 6,081,745 A | 6/2000 | Mehra | | |
| RE36,765 E | 7/2000 | Mehra | | |
| 6,169,923 B1 * | 1/2001 | Kroll | | 607/5 |
| 6,434,417 B1 * | 8/2002 | Lovett | | 600/509 |
| 6,459,932 B1 | 10/2002 | Mehra | | |
| 7,133,720 B2 | 11/2006 | Seim | | |
| 7,532,928 B2 | 5/2009 | Lang | | |
| 8,078,272 B2 * | 12/2011 | Lin | | 600/518 |
| 2002/0147468 A1 | 10/2002 | Kim et al. | | |
| 2003/0204215 A1 | 10/2003 | Gunderson et al. | | |
| 2004/0210256 A1 | 10/2004 | Musley et al. | | |
| 2004/0220630 A1 | 11/2004 | Mongeon et al. | | |
| 2005/0154421 A1 | 7/2005 | Ousdigian | | |
| 2007/0135722 A1 | 6/2007 | Lin | | |
| 2008/0051843 A1 | 2/2008 | Li et al. | | |
| 2008/0077030 A1 | 3/2008 | Ostroff et al. | | |
| 2009/0259269 A1 | 10/2009 | Brown | | |
| 2010/0241180 A1 | 9/2010 | Whitman et al. | | |
| 2011/0125041 A1 * | 5/2011 | Fischell et al. | | 600/515 |

FOREIGN PATENT DOCUMENTS

WO 2004098707 A2 11/2004

OTHER PUBLICATIONS

Search Report and Written Opinion from international application No. PCT/US2011/034271, dated Sep. 23, 2011, 18 pp.
Invitation to Pay Additional Fees from international application No. PCT/US2011/034271, dated Aug. 2, 2011, 7 pp.

* cited by examiner

*Primary Examiner* — George Manuel
*Assistant Examiner* — Robert N Wieland
(74) *Attorney, Agent, or Firm* — Michael C. Soldner

(57) ABSTRACT

Systems and methods are described for analyzing a plurality of beats after detection of a suspected cardiac arrhythmia to determine a beat discriminator, identify a beat subsequent to completion of charging of an implantable medical device by applying the beat discriminator, and synchronize delivery of a shock from the medical device to the identified beat. In some examples, identifying the beat using the beat discriminator may help to accurately synchronize the shock with a beat representative of physiological cardiac events instead of an oversensed beat, e.g., noise sensed signal that is misclassified as a cardiac beat.

24 Claims, 10 Drawing Sheets

SYNCHRONIZATION OF ELECTRICAL STIMULATION THERAPY TO TREAT CARDIAC ARRHYTHMIAS

TECHNICAL FIELD

The disclosure relates to medical devices and, more particularly, to delivery of electrical stimulation to treat a cardiac arrhythmia of a patient by medical devices.

BACKGROUND

A variety of implantable medical devices for delivering a therapy and/or monitoring a physiological condition have been clinically implanted or proposed for clinical implantation in patients. Some implantable medical devices deliver electrical stimulation to, and/or monitor conditions associated with, the heart, muscle, nerve, brain, stomach or other organs or tissue. Some implantable medical devices employ one or more elongated electrical leads carrying stimulation electrodes, sense electrodes, and/or other sensors. Implantable medical leads may be configured to allow electrodes or other sensors to be positioned at desired locations for delivery of stimulation or sensing. For example, electrodes or sensors may be carried at a distal portion of a lead, which may be implanted at the desired location. A proximal portion of the lead may be coupled to an implantable medical device housing, which may contain circuitry such as signal generation and/or sensing circuitry.

Some implantable medical devices, such as cardiac pacemakers or cardioverter-defibrillators, provide therapeutic electrical stimulation to the heart via electrodes carried by one or more implantable leads. The electrical stimulation may include signals such as pulses or shocks for pacing, cardioversion, or defibrillation. In some cases, an implantable medical device senses intrinsic depolarizations of the heart, and controls delivery of stimulation signals to the heart based on the sensed depolarizations. Upon detection of an abnormal rhythm, such as bradycardia, tachycardia or fibrillation, an appropriate electrical stimulation signal or signals may be delivered to restore or maintain a more normal rhythm. For example, in some cases, an implantable medical device may deliver pacing pulses to the heart of the patient upon detecting tachycardia or bradycardia, and deliver cardioversion or defibrillation shocks to the heart upon detecting tachycardia or fibrillation.

Implantable medical leads typically include a lead body containing one or more elongated electrical conductors that extend through the lead body from a connector assembly provided at a proximal lead end to one or more electrodes located at the distal lead end or elsewhere along the length of the lead body. The conductors connect signal generation and/or sensing circuitry within an associated implantable medical device housing to respective electrodes or sensors. Some electrodes may be used for both delivery of therapeutic signals and sensing. Each electrical conductor is typically electrically isolated from other electrical conductors and is encased within an outer sheath that electrically insulates the lead conductors from body tissue and fluids.

Medical lead bodies implanted for cardiac applications tend to be continuously flexed by the beating of the heart. Other stresses may be applied to the lead body, including the conductors therein, during implantation or lead repositioning. Patient movement can cause the route traversed by the lead body to be constricted or otherwise altered, causing stresses on the lead body and conductors. In rare instances, such stresses may fracture a conductor within the lead body. The fracture may be continuously present, or may intermittently manifest as the lead flexes and moves. Also, the wear and degradation of the insulation between the conductors may result in shorting.

Additionally, the electrical connection between medical device connector elements and the lead connector elements can be intermittently or continuously disrupted. For example, connection mechanisms, such as set screws, may be insufficiently tightened at the time of implantation, followed by a gradual loosening of the connection. Also, lead pins may not be completely inserted.

Lead fracture, disrupted connections, or other causes of short circuits or open circuits may be referred to, in general, as lead related conditions. In the case of cardiac leads, sensing of an intrinsic heart rhythm through a lead can be altered by lead related conditions. In particular, lead related conditions may cause noise in a cardiac electrogram signal received by an implantable medical device, which may be incorrectly sensed by the implantable medical device as cardiac beats.

This phenomenon is referred to as oversensing, i.e., oversensing of cardiac beats. Other causes of oversensing include other causes of non-physiologic noise in the cardiac electrogram, such as electromagnetic interference, and incorrectly characterizing a T-wave within the cardiac electrogram as a cardiac beat, which is referred to as T-wave oversensing. Oversensing may cause an implantable medical device to incorrectly detect a cardiac tachyarrhythmia, and deliver an unnecessary shock to treat the cardiac tachyarrhythmia.

SUMMARY

In general, IMDs attempt to synchronize a defibrillation or cardioversion shock to a cardiac beat. In addition to causing misidentification of a tachyarrhythmia, oversensing may also negatively affect the ability of an implantable medical device (IMD) to synchronize the delivery of a shock to a cardiac beat. In particular, an IMD may incorrectly synchronize a shock to an oversensed beat, rather than a true cardiac beat. During an episode of oversensing, delivery of an unnecessary and unsynchronized shock may be particularly undesirable.

In general, the disclosure is directed to techniques for synchronizing delivery of a shock with beats of a heart of a patient to treat a cardiac arrhythmia of the patient. Implantable medical devices for treating cardiac arrhythmias may aim to deliver electrical stimulation, e.g., pulses or shocks, synchronized to a patient's heart rhythm. Improvements in synchronization of delivery of electrical stimulation with the patient's heart rhythm may help to more effectively treat the cardiac arrhythmia of the patient.

In one example, a method comprises receiving a signal indicative of activity of a heart of a patient, detecting beats within the signal, detecting a suspected cardiac arrhythmia based on a plurality of the detected beats, initiating charging of at least one component of an implantable device configured to deliver a shock to the heart of the patient to treat the cardiac arrhythmia in response to detecting the suspected cardiac arrhythmia, analyzing the plurality of beats subsequent to the detection of the suspected cardiac arrhythmia to determine a beat discriminator, in response to completion of the charging, applying the beat discriminator to the signal to identify a beat subsequent to the completion of the charging, and synchronizing delivery of the shock to the identified beat.

In another example, a system comprises a signal generator configured to deliver a shock to a heart of a patient to treat a cardiac arrhythmia of the patient, a sensing module configured to sense a signal indicative of activity of the heart of the patient, and a processor comprising a signal receiving module configured to receive the signal, a beat detection module configured to detect beats within the signal, an arrhythmia detection module configured to detect a suspected cardiac arrhythmia based on a plurality of the detected beats, a charge initiating module configured to initiate charging of at least one component of the signal generator in response to detecting the suspected cardiac arrhythmia, a beat analysis module configured to analyze the plurality of the beats subsequent to the detection of the suspected cardiac arrhythmia to determine a beat discriminator, a beat identification module configured to, in response to completion of the charging of the signal generator, apply the beat discriminator to the signal to identify a beat subsequent to the completion of the charging of the signal generator, and a shock synchronization module configured to control the signal generator to synchronize delivery of the shock to the identified beat.

In another example, a system comprises means for receiving a signal indicative of activity of a heart of a patient, means for detecting beats within the signal, means for detecting a suspected cardiac arrhythmia based on a plurality of the detected beats, means for initiating charging of at least one component of an implantable device configured to deliver a shock to the heart of the patient to treat the cardiac arrhythmia in response to detecting the suspected cardiac arrhythmia, means for analyzing the plurality of the beats subsequent to the detection of the suspected cardiac arrhythmia to determine a beat discriminator, means for, in response to completion of the charging, applying the beat discriminator to the signal to identify a beat subsequent to the completion of the charging, and means for synchronizing delivery of the shock to the identified beat.

In another example, a computer-readable storage medium comprises instructions that cause a processor to receive a signal indicative of activity of a heart of a patient, detect beats within the signal, detect a suspected cardiac arrhythmia based on a plurality of the detected beats, initiate charging of at least one component of an implantable device configured to deliver a shock to the heart of the patient to treat the cardiac arrhythmia in response to detecting the suspected cardiac arrhythmia, analyze the plurality of the beats subsequent to the detection of the suspected cardiac arrhythmia to determine a beat discriminator, in response to completion of the charging, apply the beat discriminator to the signal to identify a beat subsequent to the completion of the charging, and synchronize delivery of the shock to the identified beat.

The details of one or more examples of the disclosure are set forth in the accompanying drawings and the description below. Other features, objects, and advantages of the disclosure will be apparent from the description and drawings, and from the claims.

DETAILED DESCRIPTION

In general, it is desirable to synchronize the delivery of a therapeutic shock, e.g., a cardioversion or defibrillation shock, to a heart with the depolarization of the ventricles of the heart.

Improvements in detection of cardiac arrhythmias have increased the efficacy of therapy in treating cardiac arrhythmias of patients. For example, more accurate detection of a cardiac arrhythmia (e.g., more accurate discrimination between time periods in which a patient is experiencing an arrhythmia and time periods in which the patient is not experiencing an arrhythmia) can facilitate delivery of therapy only during time periods in which the patient requires treatment of the cardiac arrhythmia (e.g., time periods in which the patient is experiencing an arrhythmia). However, even with improvements in detection of cardiac arrhythmias, oversensing may continue to occur (albeit less frequently, in some examples). Consequently, improving other aspects of therapy delivery, in addition to improving detection, may increase the efficacy of the delivered therapy in treating a patient's cardiac arrhythmia.

For example, improvements in synchronization of shock delivery with cardiac beats after the arrhythmia has been detected may also improve efficacy of the therapy. The examples described herein are related to improved synchronization of shock delivery with particular cardiac events, such as ventricular depolarizations, in order to more effectively treat cardiac arrhythmias of patients. The examples described herein take into account the possibility that oversensing may occur, even with improved detection techniques, and are directed to discriminating between true sensed cardiac events and sensed events that result from other types of electrical activity, which may facilitate more accurate synchronization a shock with a true cardiac event. Moreover, in situations in which oversensing does not occur (e.g., if the detection of cardiac events is accurate), the techniques described herein may also result in accurate and effective synchronization of shocks to true cardiac events.

The examples herein are described with respect to synchronization of a shock with ventricular depolarizations of the patient, which can be represented by R-waves in a cardiac electrogram (EGM) signal of the patient. In other examples, the shock may be synchronized to cardiac beats detected in another type of signal, such as an accelerometer signal, piezoelectric sensor signal, heart sound signal, pressure signal, or any signal in which electrical depolarization or mechanical contraction of the heart may be detected. Synchronizing a shock to a cardiac beat detected in such signals may be effective in synchronizing the shock to the cardiac depolarization.

Figure 1:
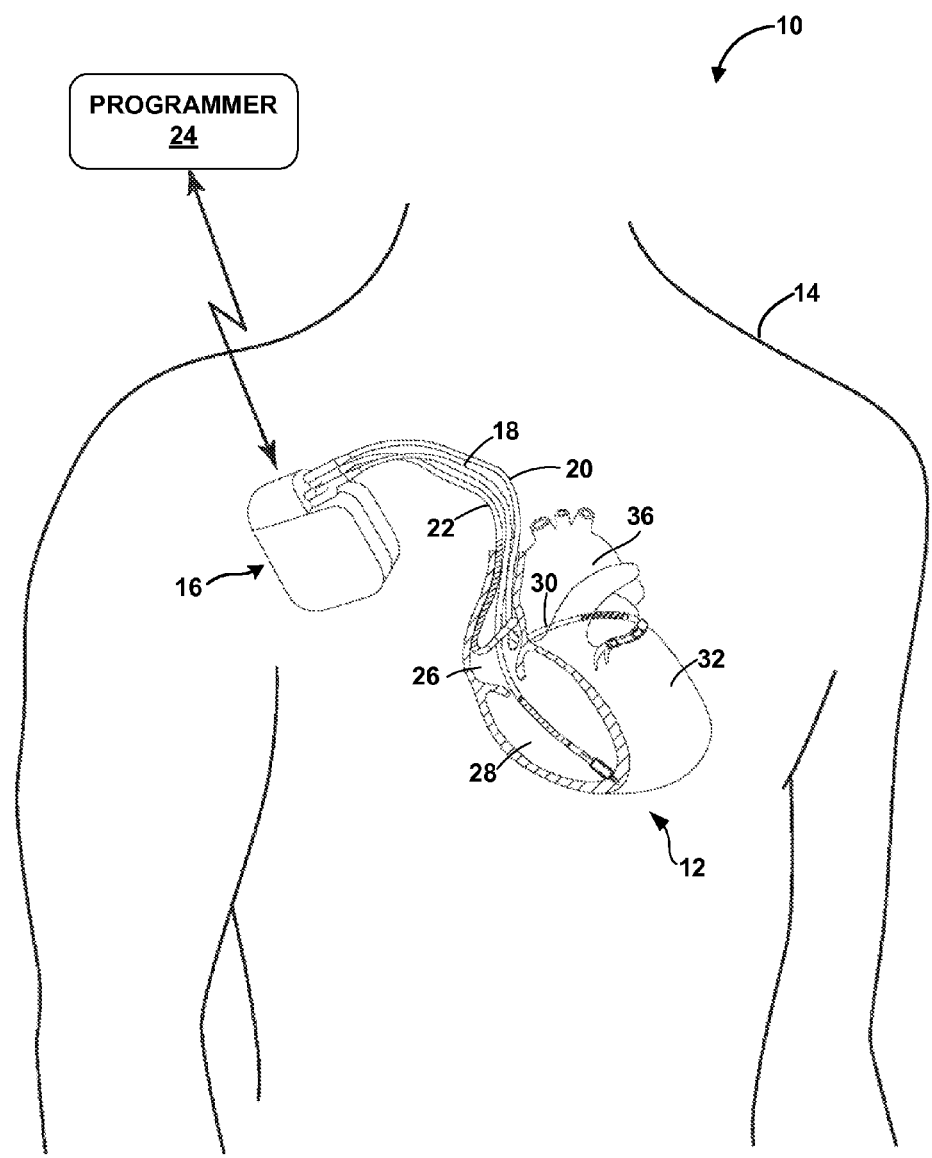
FIG. 1 is a conceptual diagram illustrating an example system comprising an implantable medical device (IMD) for sensing the electrical activity of a heart of a patient and/or delivering electrical stimulation therapy to the heart via implantable leads.

FIG. 1 is a conceptual diagram illustrating an example system 10 that monitors and provides therapy to heart 12 of patient 14. System 10 includes implantable medical device (IMD) 16, which is coupled to implantable leads 18, 20 and 22. Thus, system 10 may be referred to as an implantable medical device system. IMD 16 may be, for example, an implantable pacemaker, cardioverter, and/or defibrillator that senses electrical activity within heart 16 and provides electrical signals to heart 12 via electrodes coupled to leads 18, 20, and 22.

Leads 18, 20, 22 extend into the heart 12 of patient 14 to sense electrical activity of heart 12 and deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into right atrium 26 of heart 12. In some alternative embodiments, therapy system 10 may include an additional lead or lead segment (not shown in FIG. 1) that deploys one or more electrodes within the vena cava or other vein. These electrodes may allow alternative electrical sensing configurations that may provide improved sensing accuracy in some patients.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. In some examples, IMD 16 provides pacing pulses as part of a cardiac resynchronization therapy (CRT) or anti-tachycardia pacing therapy (ATP).

IMD 16 may also provide defibrillation therapy and/or cardioversion therapy via electrodes located on at least one of the leads 18, 20, 22. IMD 16 may detect tachyarrhythmia of heart 12, such as tachycardia or fibrillation of ventricles 28 and 32, and deliver ATP, cardioversion, or defibrillation therapy, to heart 12. In some examples, IMD 16 may be programmed to deliver a progression of therapies, e.g., ATP followed by defibrillation, or pulses shocks with increasing energy levels, until a tachyarrhythmia of heart 12 is stopped. IMD 16 detects tachycardia or fibrillation employing one or more tachycardia or fibrillation detection techniques known in the art.

In the example of FIG. 1, system 10 also includes a programmer 24. In some examples, programmer 24 may be a handheld computing device, computer workstation, or networked computing device. A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of IMD 16.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, and 22, or a power source of IMD 16.

The user may use programmer 24 to program a therapy progression, select electrodes used to deliver defibrillation shocks, select waveforms for the defibrillation shocks, or select or configure a fibrillation detection algorithm for IMD 16. The user may also use programmer 24 to program similar aspects of other therapies provided by IMD 16, such as cardioversion or pacing therapies.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

IMD 16 is an example of a device that receives a signal indicative of activity of heart 12, detects beats within the signal, detects a suspected cardiac arrhythmia based on a plurality of the detected beats, initiates charging of at least one component of IMD 16 configured to deliver a shock to heart 12 to treat the cardiac arrhythmia in response to detecting the suspected cardiac arrhythmia, analyzes the plurality of beats subsequent to the detection of the suspected cardiac arrhythmia to determine a beat discriminator, applies the beat discriminator to the signal to identify a beat subsequent to the completion of the charging in response to completion of the charging, and synchronizes delivery of the shock to the identified beat. In some examples, a processor of IMD 16, such as processor 72 (FIGS. 4 and 5), performs the techniques attributed to IMD 16 herein. Additionally, in some examples, sensing circuitry coupled to one or more electrodes may sense the signal indicative of activity of heart 12 and signal generating circuitry coupled to one or more electrodes may generate the shock used to treat the cardiac arrhythmia and deliver the shock via the one or more electrodes.

In other examples, one or more devices other than IMD 16 may, alone or in combination with IMD 16, implement the techniques described herein. For example, in some examples, external programmer 24 or another external device may receive and analyze the electrical signal sensed by IMD 16, e.g., via wireless telemetry, according to any of the techniques described herein. In addition, external programmer 24 or another external device may, through control of IMD 16, synchronize delivery of an electrical stimulation shock by IMD 16 to treat the suspected cardiac arrhythmia of patient 14.

Furthermore, although described in the context of an implantable medical device system including an implantable cardiac device, the techniques described herein may be applicable to other medical device systems including other medical devices that may be coupled to one or more leads. For example, the techniques described herein may be applicable to medical device systems in which the medical device and/or leads are not implanted, or which do not include leads.

Figure 2:
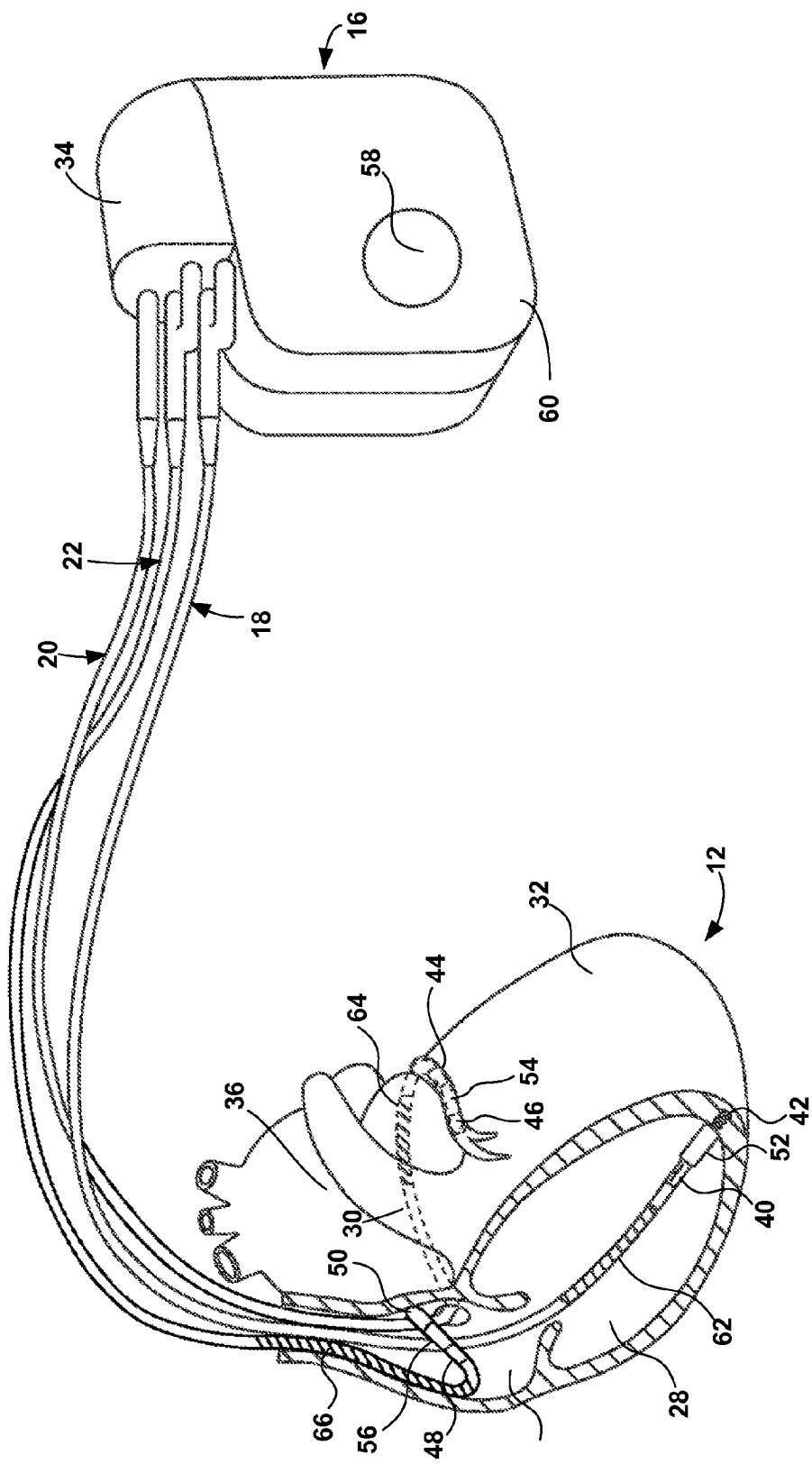
FIG. 2 is a conceptual diagram further illustrating the IMD and leads of the system of FIG. 1 in conjunction with the heart.

FIG. 2 is a conceptual diagram illustrating a three-lead IMD 16 and leads 18, 20 and 22 of therapy system 10 in greater detail. Leads 18, 20, 22 may be electrically coupled to a signal generator and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. There are no electrodes located in left atrium 36 in the illustrated example, but other examples may include electrodes in left atrium 36.

Electrodes 40, 44, and 48 may take the form of ring electrodes, and electrodes 42, 46, and 50 may take the form of extendable helix tip electrodes mounted retractably within insulative electrode heads 52, 54, and 56, respectively. In other embodiments, one or more of electrodes 42, 46, and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64, and 66 may be electrically coupled to a respective one of the coiled conductors within the lead body of its associated lead 18, 20, 22, and thereby coupled to respective ones of the electrical contacts on the proximal end of leads 18, 20, 22.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 4, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 58, 62, 64, and 66. The electrical signals are conducted to IMD 16 from the electrodes via the respective leads 18, 20, 22 or, in the case of housing electrode 58, a conductor couple to housing electrode 58. IMD 16 may sense such electrical signals via any bipolar combination of electrodes 40, 42, 44, 46, 48, 50, 58, 62, 64, and 66. Furthermore, any of the electrodes 40, 42, 44, 46, 48, 50, 58, 62, 64, and 66 may be used for unipolar sensing in combination with housing electrode 58.

Any multipolar combination of two or more of electrodes 40, 42, 44, 46, 48, 50, 58, 62, 64, and 66 may be considered a sensing electrode configuration. Usually, but not necessarily, a sensing electrode configuration is a bipolar electrode combination on the same lead, such as electrodes 40 and 42 of lead 18. On one lead having three electrodes, there may be at least three different sensing electrode configurations available to IMD 16. These sensing electrode configurations are, for the example of lead 18, tip electrode 42 and ring electrode 40, tip electrode 42 and elongated electrode 62, and ring electrode 40 and elongated electrode 62. However, some embodiments may utilize sensing electrode configurations having electrodes of two different leads. Further, a sensing electrode configuration may utilize housing electrode 58, which may provide a unipolar sensing electrode configuration. In some examples, a sensing electrode configuration may comprise multiple housing electrodes 58. In any sensing electrode configuration, the polarity of each electrode may be configured as appropriate for the application of the sensing electrode configuration.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver defibrillation shocks to heart 12 via any combination of elongated electrodes 62, 64, 66, and housing electrode 58. Electrodes 58, 62, 64, 66 may also be used to deliver cardioversion shocks to heart 12. Electrodes 62, 64, 66 may be fabricated from any suitable electrically conductive material, such as, but not limited to, platinum, platinum alloy or other materials known to be usable in implantable defibrillation electrodes.

The configuration of system 10 illustrated in FIGS. 1 and 2 is merely one example. In other examples, a system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

In addition, in other examples, a therapy system may include any suitable number of leads coupled to IMD 16, and each of the leads may extend to any location within or proximate to heart 12. For example, therapy systems may include three transvenous leads located as illustrated in FIGS. 1 and 2, and an additional lead located within or proximate to left atrium 36. As another example, therapy systems may include a single lead that extends from IMD 16 into right atrium 26 or right ventricle 28, or two leads that extend into a respective one of the right ventricle 26 and right atrium 26. An example of the latter type of therapy system is shown in FIG. 3.

Figure 3:
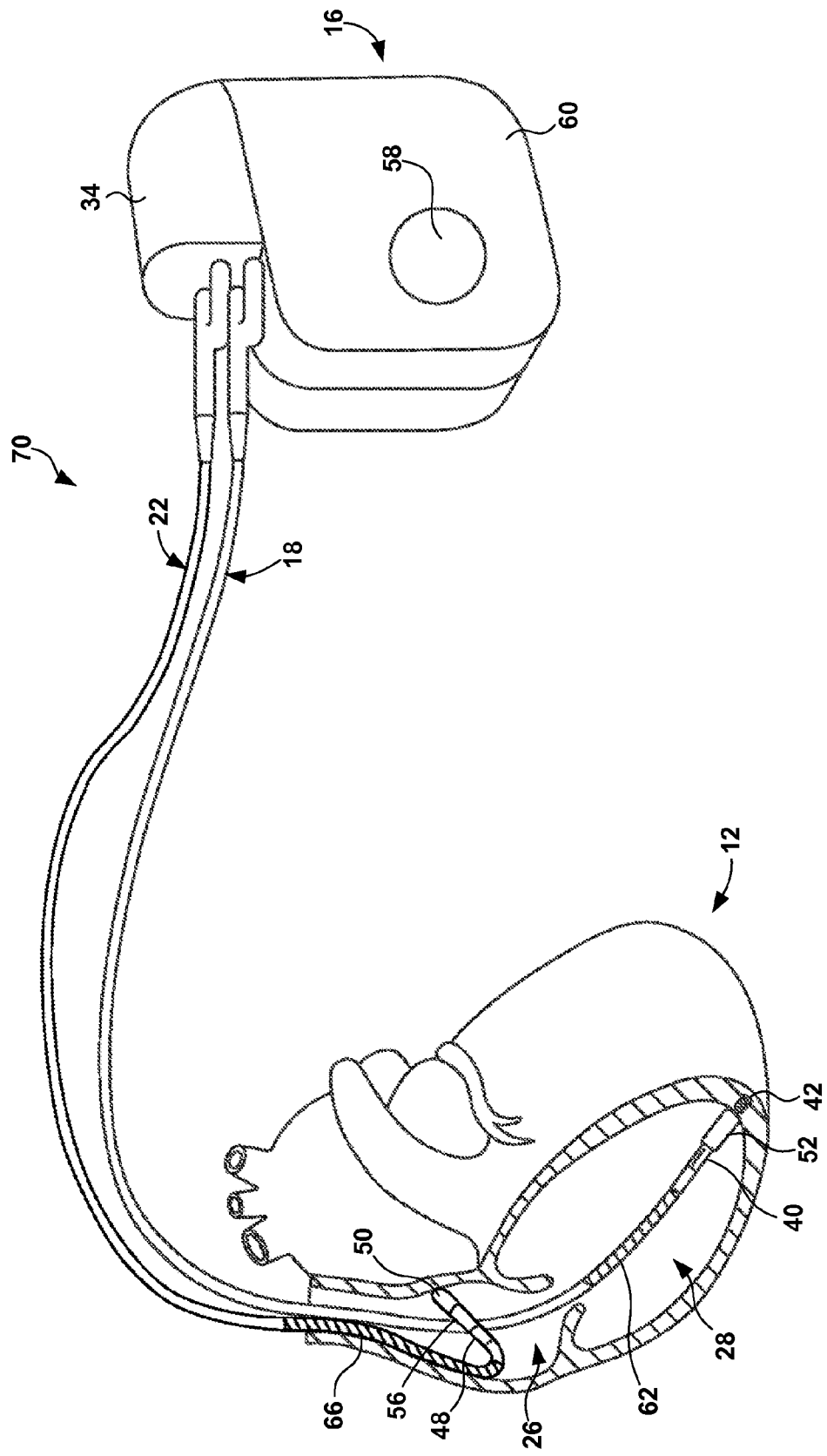
FIG. 3 is a conceptual diagram illustrating another example therapy system comprising the IMD of FIG. 1 coupled to a different configuration of leads.

FIG. 3 is a conceptual diagram illustrating therapy system 70, which is similar to therapy system 10 of FIGS. 1 and 2, but includes two leads 18, 22, rather than three leads. Leads 18, 22 are implanted within right ventricle 28 and right atrium 26, respectively. Therapy system 70 shown in FIG. 3 may be useful for providing pacing, cardioversion and defibrillation therapy to heart 12. Synchronizing delivery of a shock according to the techniques described herein may also be performed by or with respect to system 70.

Figure 4:
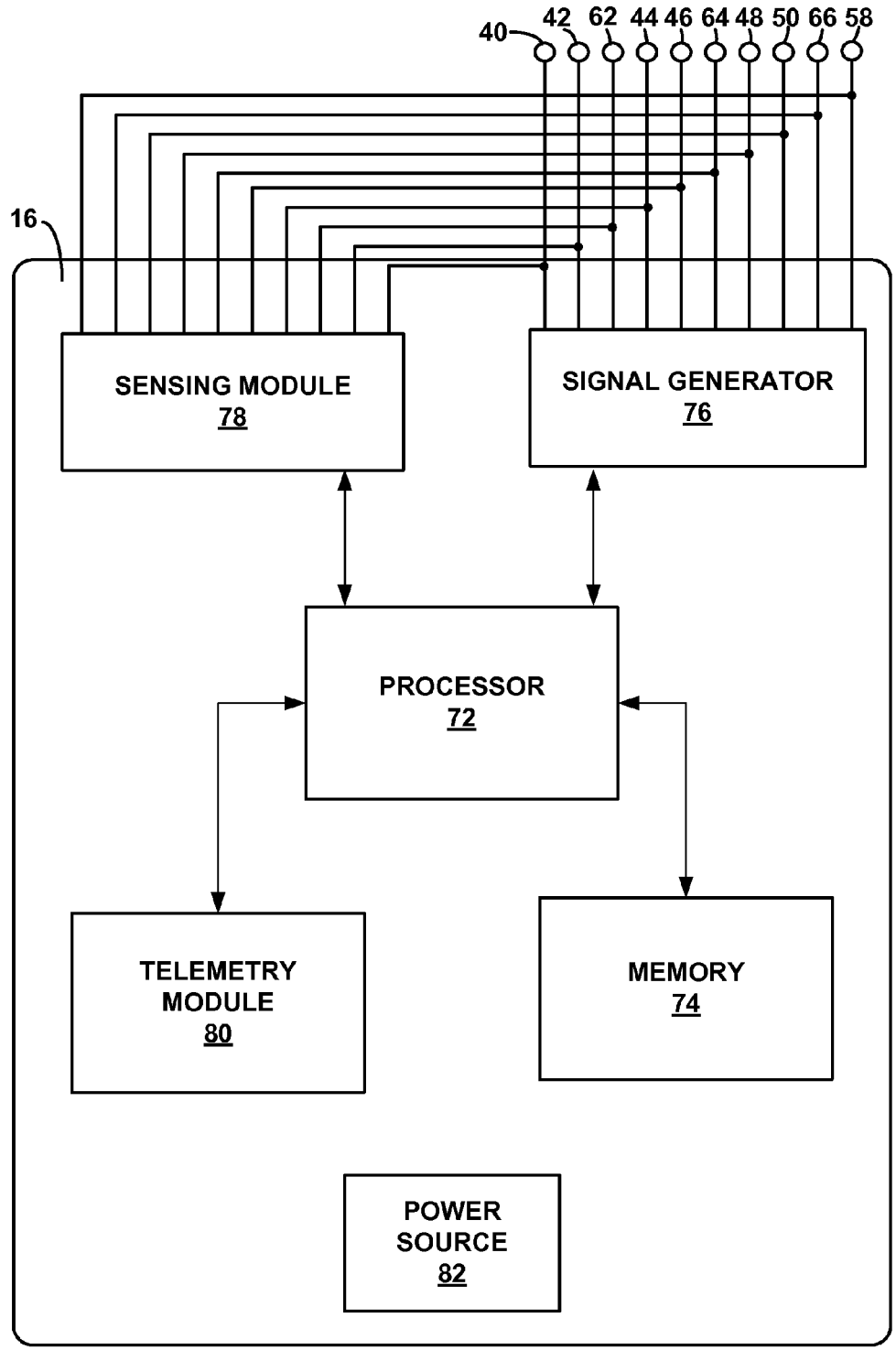
FIG. 4 is a functional block diagram illustrating an example configuration of the IMD of FIG. 1.

FIG. 4 is a functional block diagram illustrating an example configuration of IMD 16. In the example illustrated by FIG. 4, IMD 16 includes a processor 72, memory 74, signal generator 76, sensing module 78, telemetry module 80, and power source 82. Memory 74 may include computer-readable instructions that, when executed by processor 72, cause IMD 16 and processor 72 to perform various functions attributed to IMD 16 and processor 72 herein. Memory 84 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 72 may include any one or more of a microprocessor, a controller, a digital signal processor (DSP), an application specific integrated circuit (ASIC), a field-programmable gate array (FPGA), or equivalent discrete or integrated logic circuitry. In some examples, processor 72 may include multiple components, such as any combination of one or more microprocessors, one or more controllers, one or more DSPs, one or more ASICs, or one or more FPGAs, as well as other discrete or integrated logic circuitry. The functions attributed to processor 72 herein may be embodied as software, firmware, hardware or any combination thereof. Processor 72 controls signal generator 76 to deliver stimulation therapy to heart 12. Processor 72 may control signal generator 76 to deliver stimulation according to selected algorithms and parameter values, which may be stored in memory 74.

Signal generator 76 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16A. Signal generator 76 is configured to generate and deliver electrical stimulation therapy to heart 12. For example, signal generator 76 may deliver defibrillation or cardioversion shocks to heart 12 via at least two electrodes 58, 62, 64, 66. Signal generator 76 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 76 delivers pacing, cardioversion, or defibrillation stimulation in the form of electrical pulses. In other examples, signal generator 76 may deliver one or more of these types of stimulation in the form of other signals, such as sine waves, square waves, or other substantially continuous time signals.

Signal generator 76 may include a switch module and processor 72 may use the switch module to select, e.g., via a data/address bus, which of the available electrodes are used to deliver pacing, cardioversion, or defibrillation. The switch module may include a switch array, switch matrix, multiplexer, or any other type of switching device suitable to selectively couple the therapy signal to selected electrodes.

Sensing module 78 monitors signals from at least one of electrodes 40, 42, 44, 46, 48, 50, 58, 62, 64 or 66 in order to monitor electrical activity of heart 12. Sensing module 78 may also include a switch module to select which of the available electrodes are used to sense the heart activity. In some examples, processor 72 may select the electrodes that function as sense electrodes, or the sensing electrode configuration, via the switch module within sensing module 78, e.g., by providing signals via a data/address bus.

Sensing module 78 may include multiple detection channels, each of which may comprise an amplifier. The detection channels may receive cardiac signals. Some detection channels may be configured to detect particular cardiac events within the signals, such as R-waves or P-waves, and provide indications of the occurrences of such events to processor 72. One or more other detection channels may provide the signals to an analog-to-digital converter, for processing or analysis of the signals by processor 72. In response to the control signals from processor 72, the switch module of sensing module 78 may couple selected electrodes to each of the detection channels. Detection of an R-wave by a sensing channel of sensing module 78 may be an example of detection of a cardiac beat.

In some examples, sensing module 78 may be configured such that the multiple detection channels sense the same electrical activity, e.g., right ventricular activity, via multiple electrode combinations. Processor 72 may compare the signals to one another and, more particularly, the number of detected cardiac events within each signal, to determine whether a particular electrode combination more accurately detects true cardiac events, as will be described in further detail below with respect to FIG. 6.

Processor 72 may include a timing and control module, which may be embodied as hardware, firmware, software, or any combination thereof. The timing and control module may comprise a dedicated hardware circuit, such as an ASIC, separate from other components of processor 72, or a software module executed by a component of processor 72. If IMD 16 is configured to generate and deliver pacing pulses to heart 12, the timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber that is sensed, and the third letter may indicate the chamber in which the response to sensing is provided.

Intervals defined by the timing and control module within processor 72 may include atrial and ventricular pacing escape intervals, refractory periods during which sensed P-waves and R-waves are ineffective to restart timing of the escape intervals, and the pulse widths of the pacing pulses. As another example, the timing and control module may define a blanking period, and provide signals to sensing module 78 to blank one or more channels, e.g., amplifiers, for a period during and after delivery of electrical stimulation to heart 12. The durations of these intervals may be determined by processor 72 in response to stored data in memory 74. The timing and control module of processor 72 may also determine the amplitude of the cardiac pacing pulses.

During pacing, escape interval counters within the timing and control module of processor 72 may be reset upon sensing of R-waves and P-waves with detection channels of sensing module 78. Signal generator 76 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. Processor 72 may reset the escape interval counters upon the generation of pacing pulses by signal generator 76, and thereby control the basic timing of cardiac pacing functions, including anti-tachyarrhythmia pacing.

In some examples, a portion of memory 74 may be configured as a plurality of circular buffers, capable of holding series of measured intervals, which may be analyzed by processor 72 in response to the occurrence of a pace or sense interrupt to determine whether the patient's heart 12 is presently exhibiting atrial or ventricular tachyarrhythmia. In some examples, an arrhythmia detection method may include any suitable tachyarrhythmia detection algorithms. In one example, processor 72 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998, or in U.S. patent application Ser. No. 10/755,185, filed Jan. 8, 2004 by Kevin T. Ousdigian, entitled "REDUCING INAPPROPRIATE DELIVERY OF THERAPY FOR SUSPECTED NON- LETHAL ARRHYTHMIAS." U.S. Pat. No. 5,545,186 to Olson et al., U.S. Pat. No. 5,755,736 to Gillberg et al., and U.S. patent application Ser. No. 10/755,185 by Kevin T. Ousdigian are incorporated herein by reference in their entireties. However, other arrhythmia detection methodologies may also be employed by processor 72 in other examples.

The various components of IMD 16 are coupled to power source 82, which may include a rechargeable or non-rechargeable battery. A non-rechargeable battery may be capable of holding a charge for several years, while a rechargeable battery may be inductively charged from an external device, e.g., on a daily or weekly basis.

Figure 5:
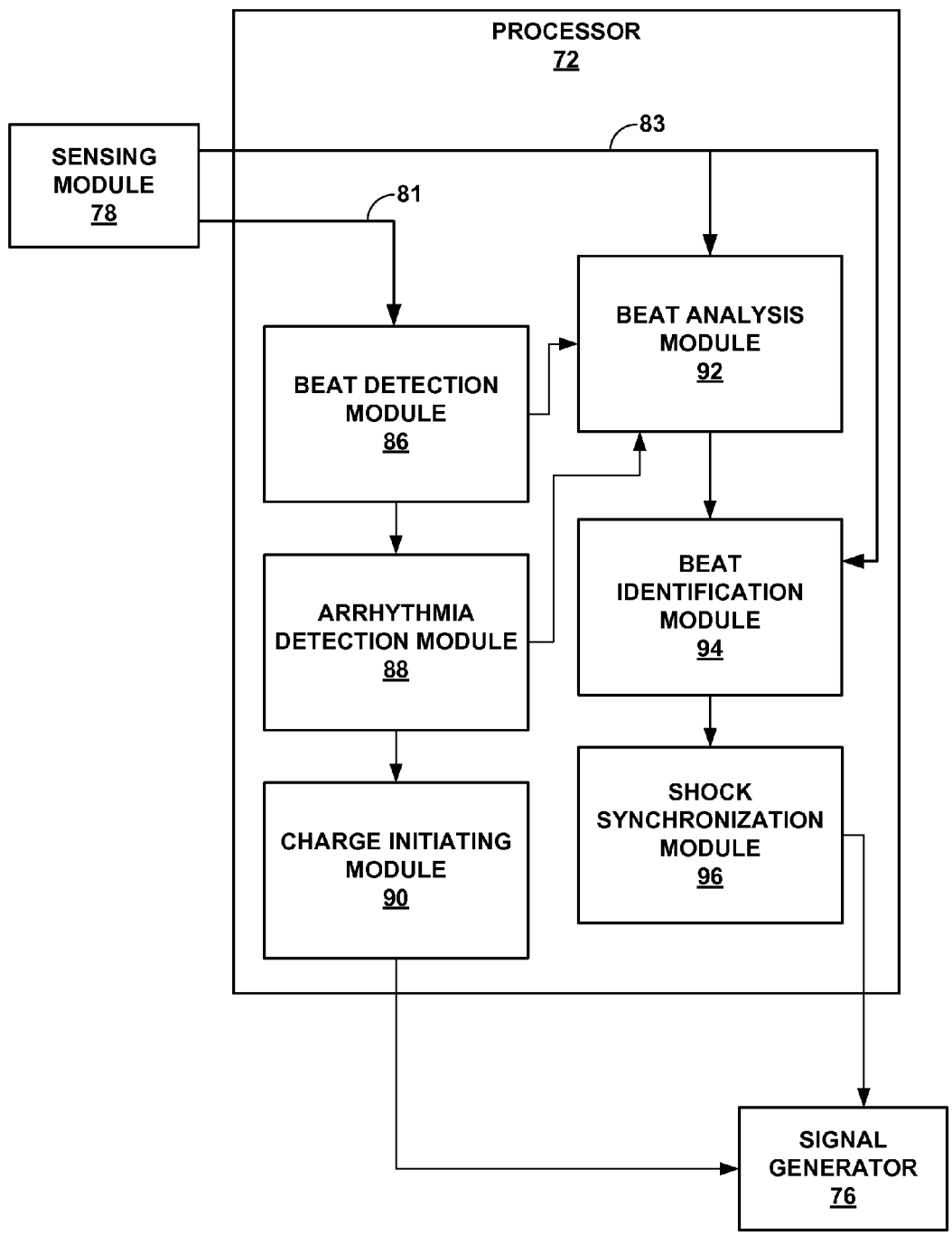
FIG. 5 is a functional block diagram further illustrating the sensing module, the signal generator, and the processor of the IMD of FIG. 4.

FIG. 5 is a functional block diagram illustrating an example configuration of processor 72, signal generator 76, and sensing module 78 of IMD 16 (FIG. 4). In the example illustrated in FIG. 5, processor 72 includes a beat detection module 86, arrhythmia detection module 88, charge initiating module 90, beat analysis module 92, beat identification module 94, and shock synchronization module 96. In some examples, the modules of processor 72 may interact with signal generator 76 and sensing module 78 as described in further detail below and as indicated by the arrows in FIG. 5.

In the example illustrated in FIG. 5, processor 72 is configured to synchronize delivery of an electrical signal to heart 12 of patient 14 with the heart rhythm of patient 14 in order to treat a cardiac arrhythmia of patient 14. As discussed above, signal generator 76 can deliver a therapeutic electrical signal to heart 12 via one or more of electrodes 40, 42, 44, 46, 48, 50, 58, 62, or 66 to treat the cardiac arrhythmia. As discussed above, sensing module 78 can sense electrical activity of heart 12 via one or more of electrodes 40, 42, 44, 46, 48, 50, 58, 62, or 66, sense R-waves, i.e., cardiac beats, and generate a signal indicative of the cardiac electrical activity, e.g., a cardiac electrogram.

In the example illustrated in FIG. 5, processor 72 receives indications of the occurrences of R-waves 81 from sensing module 78, e.g., from a detection channel of the sensing module. Processor 72 also receives a cardiac electrogram signal 83 representative of the electrical activity of the ventricles of heart 12 from sensing module 78.

In the example of FIG. 5, beat detection module 86 receives the indications of the occurrences of R-waves 81 from sensing module 78, and detects the timing of cardiac beats of heart 12 based on the indications. In other examples, beat detection module 86 may receive cardiac electrogram 83, and detect the R-waves therein using signal processing techniques. Furthermore, in other examples, beat detection module 86 may be configured to detect the timing of cardiac beats in other types of signals, such as accelerometer signals or pressure signals.

Arrhythmia detection module 88 may receive indications of the detection of beats from beat detection module 86. Arrhythmia detection module 88 may then determine intervals between the detected beats, and detect arrhythmia, e.g., tachyarrhythmia, based on the determined intervals. In some examples, arrhythmia detection module 88 detects a cardiac arrhythmia if some or all of the beats detected by beat detection module 86 occur at a rate outside of a range indicative of normal cardiac activity. For example, arrhythmia detection module 88 detects a tachyarrhythmia if patient 14 is experiencing or has experienced a substantially high heart rate compared to a heart rate indicative of normal activity of heart 12. In other examples, arrhythmia detection module 88 may detect a cardiac arrhythmia using any other suitable technique. For example, arrhythmia detection module 88 may additionally or alternatively receive cardiac electrogram 83 and detect cardiac arrhythmia based on the morphology or other features of the cardiac electrogram. In response to arrhythmia detection module 88 detecting the cardiac arrhythmia, charge initiating module 90 initiates charging of a component of IMD 16 responsible for delivering a shock to heart 12 to treat the cardiac arrhythmia. For example, signal generator 76 may include a capacitor or another component that requires charging before signal generator 76 can deliver an electrical shock to heart 12. Consequently, charge initiating module 90 controls signal generator 76 to initiate charging of the component in preparation for delivery of a shock to heart 12 to treat the tachyarrhythmia after arrhythmia detection module 88 has detected the tachyarrhythmia.

In addition, subsequent to arrhythmia detection module 88 detecting the cardiac arrhythmia, beat analysis module 92 analyzes a plurality of the detected beats to determine a beat discriminator. In some examples, beat analysis module 92 receives an indication of the detection of tachyarrhythmia by arrhythmia detection module 88, and indicates the analysis of the beats in response to this indication. Additionally, beat analysis module 92 may receive cardiac electrogram signal 83, and may analyze the detected cardiac beats within cardiac electrogram signal 83. As illustrated in FIG. 5, beat analysis module 92 may receive indications of the timing of detected beats from beat detection module 86 to facilitate identification of the detected beats within cardiac electrogram signal 83.

In some examples, cardiac electrogram signal 83 may include beats that are indicative of actual cardiac events and, additionally, beats that are oversensed, e.g., indicative of noise or T-waves. The beat discriminator may define any parameter that allows IMD 16 and, more specifically, processor 72 to distinguish between portions of the electrical signal indicative of actual cardiac events (e.g., ventricular depolarizations represented by R-waves in an ECG signal) and portions of the electrical signal indicative of the other electrical activity, such as electrical noise. That is, using the beat discriminator, processor 72 may distinguish between electrical signal characteristics indicative of actual cardiac events or beats and electrical signal characteristics indicative of other electrical activity.

Beat identification module 94 determines that charging of the one or more components of signal generator 76 is complete. Subsequently, beat identification module 94 applies the beat discriminator to the cardiac electrogram signal 83 to identify a true beat, i.e., a non-oversensed beat. That is, after completion of charging, sensing module 78 continues to sense the electrical signal indicative of activity of heart 12, and beat identification module 94 applies the beat discriminator to cardiac electrogram 83 in order to identify a beat that is indicative of a cardiac event. In response to identification of a beat by beat identification module 94, shock synchronization module 96 controls signal generator 76 (the components of which are charged for delivery of electrical stimulation) to synchronize delivery of an electrical shock to heart 12 to the identified beat to treat the cardiac tachyarrhythmia of patient 14. In this way, delivery of a shock may be accurately synchronized to a beat of heart 12.

In some examples, processor 72 may not include a separate module for identifying a beat for synchronization, e.g., beat identification module 94. Instead, beat analysis module 92 may modify the sensitivity of a detection channel within sensing module 78 to identify beats that meet the criteria of the beat discriminator. For example, in examples in which the beat discriminator comprises an amplitude threshold value (e.g., as described below with respect to FIGS. 7-9) beat analysis module 92 may decrease the sensitivity of the detection channel based on an amplitude threshold value that facilitates distinction between beats with amplitude values indicative of authentic physiological activity and beats with amplitude values indicative of other electrical activity, such as electrical noise.

Figure 6:
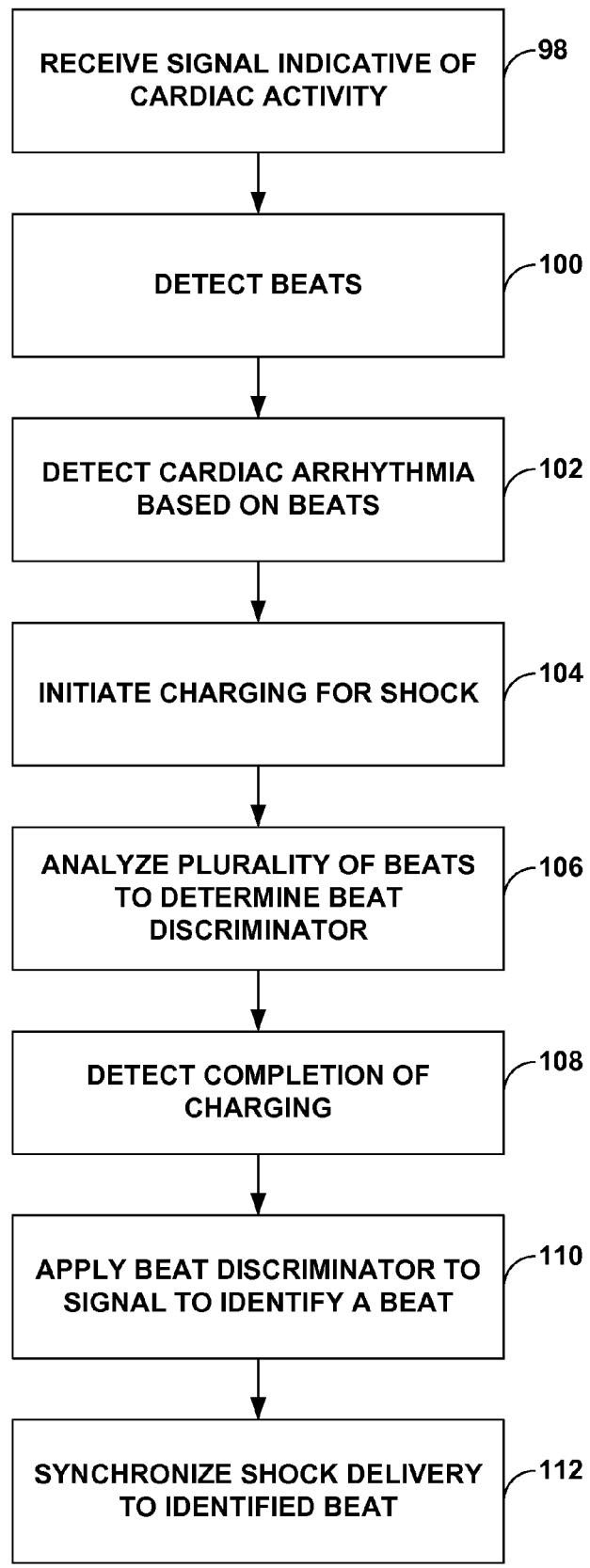
FIG. 6 is a flow diagram illustrating an example technique for synchronizing delivery of a shock to treat a cardiac arrhythmia.

FIG. 6 is a flow diagram illustrating an example technique for synchronizing delivery of an electrical shock to treat a cardiac arrhythmia of patient 14. While FIG. 6 is described as being performed by processor 72, in other examples, a processor of another device described herein, e.g., programmer 24, can automatically perform any part of the technique shown in FIG. 6 alone or with the aid of a user.

In the example illustrated in FIG. 6, processor 72 receives a signal indicative of activity of heart 12 (98). In some examples, processor 72 receives a cardiac electrogram signal, e.g., cardiac electrogram 83, from sensing module 78. In some examples, processor 72 receives the signal continuously as one or more of electrodes 40, 42, 44, 46, 48, 50, 58, 62, or 66 sense the signal.

Processor 72 detects one or more beats in the signal (100). In some examples, processor 72 receives indications of the occurrences of R-waves in the EGM signal, and detects a beat each time an R-wave occurs.

Beat detection module 86 of processor 72 analyzes the signal and, in particular, the detected beats to determine whether patient 14 is experiencing a cardiac arrhythmia. If beat detection module 86 detects abnormalities in the beats, arrhythmia detection module 88 detects a cardiac arrhythmia of patient 14 (102). In some examples, if the rate or frequency of the detected beats, e.g., the heart rate of patient 14, is faster or slower than a predetermined normal threshold value, arrhythmia detection module 88 determines that patient 14 is experiencing a cardiac arrhythmia. In response to determining that patient 14 is experiencing a cardiac arrhythmia, charge initiating module 90 initiates charging of one or more components of IMD 16 for delivery of a shock (104). For example, IMD 16 may be an implantable cardioverter defibrillator (ICD), and signal generator 76 may include one or more capacitors or other components that require charging before cardioversion or defibrillation therapy can be delivered to heart 14. Consequently, upon detecting a cardiac arrhythmia, charge initiating module 90 may initiate charging of the one or more capacitors in order to prepare IMD 16 for delivery of electrical stimulation therapy to patient 14.

In addition to charge initiating module 90 initiating charging, in response to determining that patient 14 is experiencing a cardiac arrhythmia, beat analysis module 92 analyzes one or more beats of the electrical signal to determine a beat discriminator (106). As discussed previously, the electrical signal may include beats that are indicative of actual physiologic events and beats that result from other electrical activity, such as electrical noise, that can still be detected by processor 72. The beat discriminator may be a parameter or characteristic that allows processor 72 to distinguish between beats that are indicative of actual physiological activity and beats that are indicative of other electrical activity. In some examples, beat analysis module 92 analyzes the beats to determine the beat discriminator during charging of the one or more components of IMD 16.

Processor 72 may determine that charging of the one or more components of IMD 16 is complete, e.g., that IMD 16 is prepared to deliver electrical stimulation to heart 12 (108). In response to completion of charging, beat identification module 94 applies the beat discriminator to the electrical signal to identify particular types of beats, e.g., beats indicative of cardiac events that result from authentic cardiac activity, after completion of charging (110). For example, the beat discriminator may define one or more criteria that is indicative of authentic electrical activity of heart 12 and, more specifically, of a particular type of cardiac event. Beat identification module 94 may apply the beat discriminator to the signal and identify a beat that meets the beat discriminator criteria such that processor 72 can accurately and effectively synchronize shock delivery to a true cardiac beat.

In response to identification of a beat, shock synchronization module 96 may control signal generator 76 to deliver a shock to heart 12 synchronized with the identified beat (112). As discussed previously, it may be desirable to synchronize delivery of a therapy shock to a particular portion of the cardiac cycle, such as to a ventricular depolarization. Using the technique in illustrated in FIG. 6, processor 72 can ensure that a shock is accurately delivered to heart 12 synchronously with authentic physiological activity.

In some examples, subsequent to synchronization of the shock with the identified beat, processor 72 discards or resets the beat discriminator. In some examples, the beat discriminator is not reused to identify a beat for delivery of a shock in response to a subsequent cardiac arrhythmia. Furthermore, in some examples, the beat discriminator is not used to detect beats for detecting arrhythmias or other purposes.

Although in the examples described herein beat identification module 94 identifies a beat using the beat discriminator and shock synchronization module 96 synchronizes a shock to the identified beat, in other examples, beat identification module 94 may not identify a beat using the beat discriminator and, consequently, shock synchronization module 96 may not synchronize a shock to the beat. For example, beat identification module 94 may not detect a beat that meets the criteria of the beat discriminator within a predetermined amount of time after charging of IMD 16 is complete. In these examples, shock synchronization module 96 may control signal generator 76 to deliver a shock that is unsynchronized, e.g., not synchronized with a beat, or may disregard the beat discriminator and control signal generator 76 to deliver a shock that is synchronized to any detected beat, e.g., any beat detected by sensing module 78.

Although not illustrated in the flow diagram of FIG. 6, in some examples processor 72 may receive and analyze more than one signal indicative of cardiac activity of patient 14, and select the most appropriate signal for subsequent analysis by processor 72 according to the technique illustrated in FIG. 6. For example, as mentioned above with respect to FIG. 4, sensing module 78 may include multiple detection channels configured to sense electrical activity and generate an electrical signal, e.g., an EGM, indicative of the electrical activity. Processor 72 may detect beats within each of the signals and compare the number of beats detected within each signal to one another. In some examples, processor 72 identifies the most appropriate signal for analysis based on selecting the signal that exhibits the most appropriate number of beats relative to the amount of time over which the signal was sensed.

For example, with respect to lead 18 illustrated in FIG. 2, sensing module 78 may detect a first electrical signal via an electrode combination that includes electrodes 40 and 42, a second signal via an electrode combination that includes electrodes 42 and 62, and a third signal via an electrode combination that includes electrodes 42 and 58. Processor 72 may subsequently apply one or more predetermined criteria to the first, second, and third signals to select the most appropriate signal for analysis. For example, processor 72 may identify the signal that yields the fewest beats amongst signals that have at least a minimum number of beats. The minimum number of beats required for a signal to be considered may be, for example, equal to the number of seconds for which the signal was monitored minus two.

As an example, processor 72 may detect 14 beats within the first signal, 5 beats within the second signal, and 10 beats within the third signal, where the first, second, and third signals were sensed over a time period of approximately 7 seconds. Processor 72 may subsequently determine that the second signal exhibits the fewest beats but at least the number of beats equal to the number of seconds over which the signal was sensed minus two seconds, and select the second signal for analysis via the technique illustrated in FIG. 6.

Figure 7:
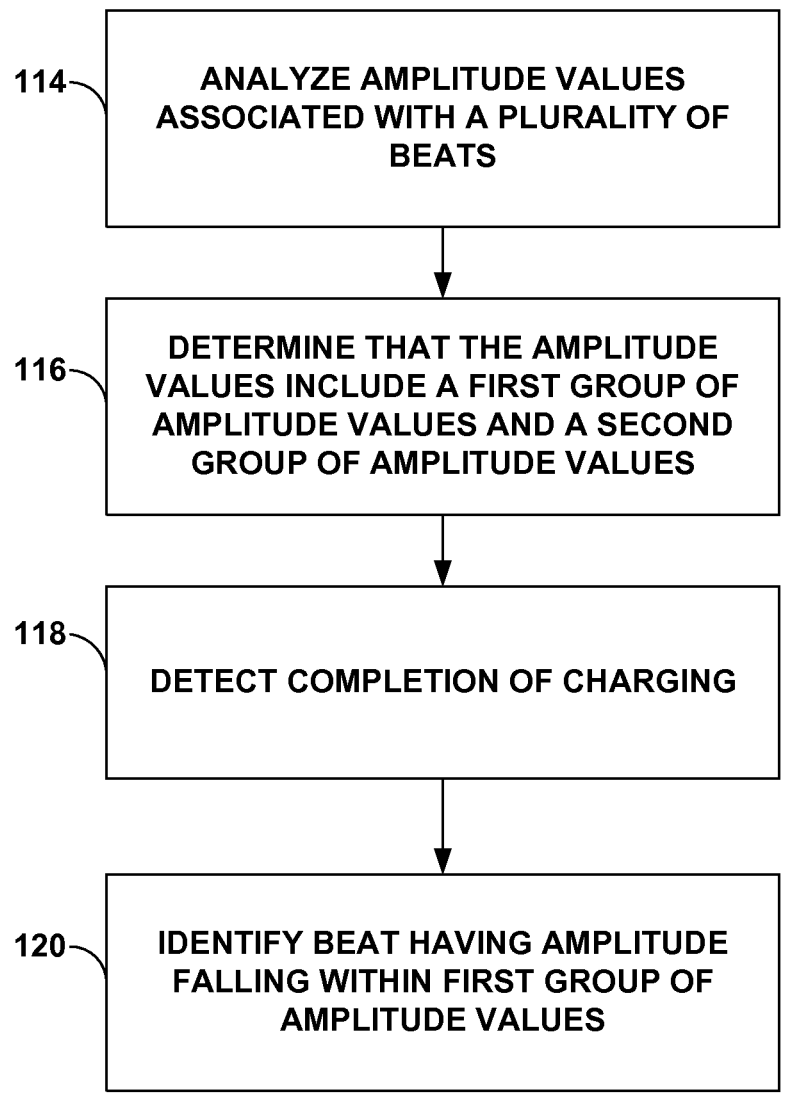
FIG. 7 is a flow diagram illustrating an example technique for analyzing a plurality of beats detected in an electrical signal.

FIG. 7 is a flow diagram illustrating an example technique for analyzing a plurality of beats indicative of a suspected cardiac arrhythmia to determine a beat discriminator. While FIG. 7 is described as being performed by processor 72, in other examples, a processor of another device described herein, e.g., programmer 24, can automatically perform any part of the technique shown in FIG. 7 alone or with the aid of a user.

In the example technique illustrated in FIG. 7, beat analysis module 92 analyzes amplitude values associated with the plurality of beats in a portion of the signal indicative of the suspected cardiac arrhythmia in order to determine the beat discriminator (114). That is, each of the detected beats may be characterized by a particular amplitude value, e.g., a peak amplitude of the beat, and beat analysis module 92 may analyze the amplitude values to determine one or more features related to amplitude that allows beat identification module 94 or another module of processor 72 to distinguish between detected beats resulting from authentic cardiac activity and detected beats resulting from other electrical activity, such as electrical noise.

In examples in which the beats are detected based on detection of R-waves (indicative of ventricular depolarizations of heart 12), the amplitude values analyzed by beat analysis module 92 may be the amplitude values defining each of the detected R-waves, e.g., the peak amplitude values of the R-waves.

In the example technique illustrated in FIG. 7, beat analysis module 92 determines that the amplitude values defining R-waves in the portion of the signal that includes the suspected cardiac arrhythmia include a first group of amplitude values and a second group of amplitude values (116). For example, beat analysis module 92 may identify two groups of beats, each defined by amplitude values that are distinguishable from one another based on one or more features. That is, beat analysis module 92 may analyze the amplitude values and determine that some of the amplitude values fall within a first group of amplitude values distinguishable from the second group of amplitude values. As an example, as described in further detail below with respect to FIG. 8, beat analysis module 92 may determine that each of the amplitude values in the first group of amplitude values exceeds each of the amplitude values in the second group of amplitude values by at least a predetermined value. In some examples, the first group of amplitude values at least partially represents a group of physiological cardiac events of the patient and the second group of amplitude values at least partially represents other electrical activity, such as electrical noise.

Processor 72 subsequently determines that charging of one or more components of signal generator 76 is complete (118), which may signify that IMD 16 is prepared to deliver electrical stimulation therapy to heart 12. Beat identification module 94 of processor 72 continues to receive the signal indicative of activity of heart 12 from sensing module 78 and, in response to completion of charging, applies the beat discriminator to the signal to determine when to deliver an electrical stimulation shock to heart 12. Specifically, beat identification module 94 analyzes the electrical signal, applies the beat discriminator, and identifies a beat having an amplitude falling with the first group of amplitude values (120). In accordance with the technique illustrated in FIG. 6, shock synchronization module 96 controls signal generator 76 to deliver an electrical shock to heart 12 synchronized to the identified beat to treat the cardiac arrhythmia of patient 14.

Figure 8:
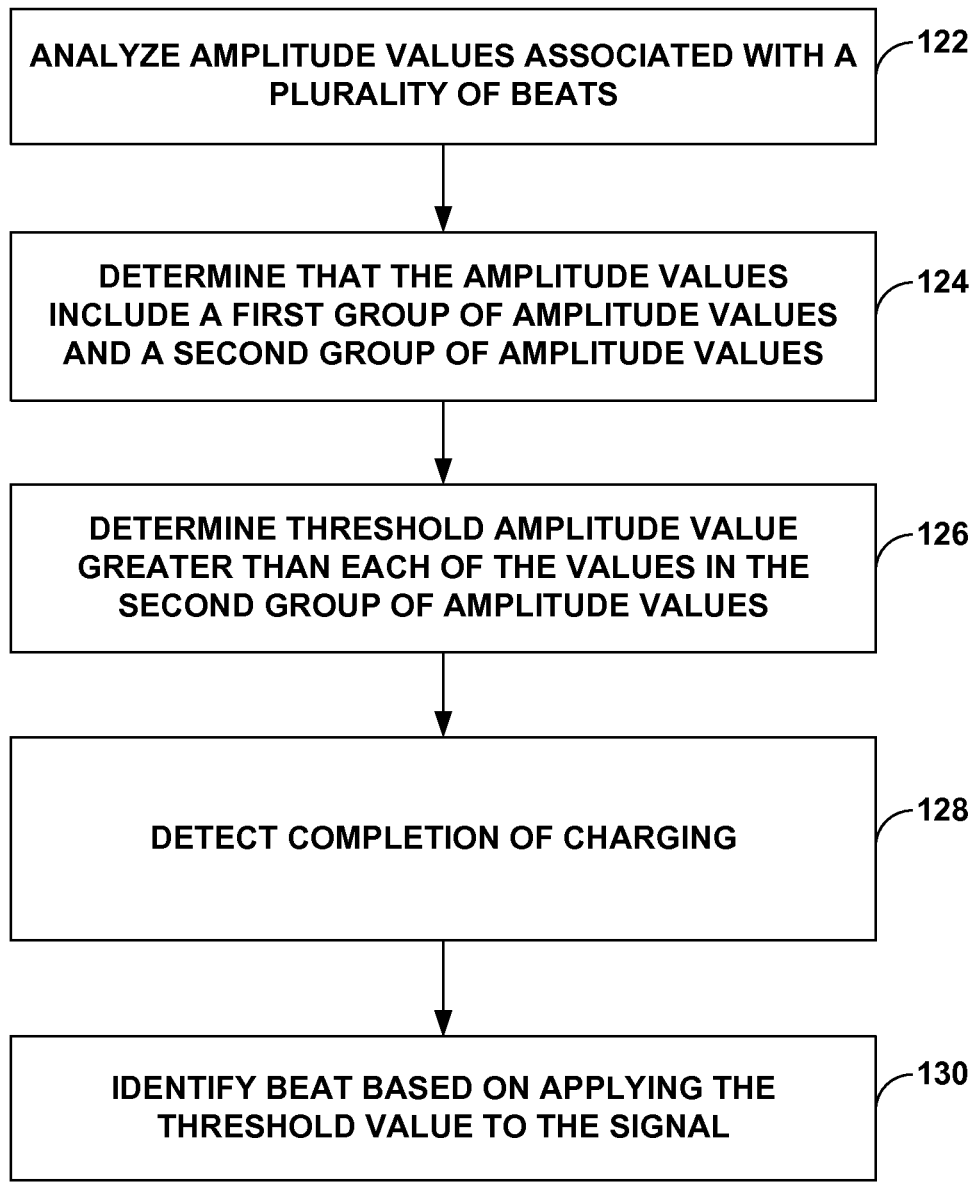
FIG. 8 is a flow diagram illustrating another example technique for analyzing a plurality of beats detected in an electrical signal.

FIG. 8 is a flow diagram illustrating another example technique for analyzing a plurality of beats indicative of a suspected cardiac arrhythmia to determine a beat discriminator. While FIG. 8 is described as being performed by processor 72, in other examples, a processor of another device described herein, e.g., programmer 24, can automatically perform any part of the technique shown in FIG. 8 alone or with the aid of a user.

In the example technique illustrated in FIG. 8, beat analysis module 92 analyzes amplitude values, e.g., peak amplitude values, associated with the plurality of beats in a portion of the signal indicative of the suspected cardiac arrhythmia in order to determine the beat discriminator (122). As discussed with respect to FIG. 7, each of the amplitude values may define the peak amplitude of a detected R-wave in the signal, and beat analysis module 92 may analyze the plurality of amplitude values, e.g., by searching for patterns, or distinguishing characteristics.

Beat analysis module 92 determines that the plurality of amplitude values includes a first group of amplitude values and a second group of amplitude values (124), e.g., first and second amplitude groups distinguishable from one another by one or more features, using any suitable technique. For example, in some examples, beat analysis module 92 may identify the first and second groups of amplitude values by determining that each of the amplitude values of the first group exceeds each of the amplitude values of the second group by at least a predetermined value. That is, beat analysis module 92 may analyze the plurality of amplitude values and determine that a first group of amplitude values generally have higher amplitudes than a second group of amplitude values. Beat analysis module 92 may subsequently determine the difference in amplitude values between the lowest amplitude value in the first group and the highest amplitude value in the second group and compare the difference to the predetermined value. If the difference meets or exceeds the predetermined value, beat analysis module 92 may characterize the first and second groups of amplitude values. As an example, in some examples, beat analysis module 92 may identify the first and second groups of amplitude values if each of the amplitude values of the first group of amplitude values exceeds each of the amplitude values of the second group of amplitude values by approximately 0.5 milliVolts (mV).

In the example technique illustrated in FIG. 8, beat analysis module 92 subsequently identifies or determines a threshold amplitude value that is greater than each of the amplitude values in the second group of amplitude values (126). As discussed above with respect to FIG. 7, in some examples, the first group of amplitude values may be derived from portions of the electrical signal representative of suspected authentic cardiac activity and the second group of amplitude values may be derived from portions of the electrical signal representative of suspected other types of electrical activity, such as electrical noise. Consequently, the threshold amplitude value determined by processor 72 may help to identify amplitude values representative of suspected authentic cardiac activity.

In one example, beat analysis module 92 stores peak amplitude values of beats detected during charging, e.g., in an array. Beat analysis module 92 may then order the amplitude values by size, and compare adjacent amplitude values in the sizedbased ordering to determine if the difference between any adjacent pair of amplitude values is greater than a predetermined threshold value, e.g., 0.5 mV. If a pair of amplitude values meeting this criteria is identified, beat analysis module 92 may divide the amplitude values into a first group that includes the greater of the pair and amplitude values above the greater amplitude value of the pair, and a second group that includes the lesser of the pair, and amplitude values below the lesser of the pair. Beat analysis module 92 may select the lesser amplitude of the pair, the greater amplitude of the pair, or some value therebetween or determined from one of these values as the threshold amplitude value, i.e., beat discriminator.

Processor 72 subsequently determines that charging of one or more components of signal generator 76 is complete (128), which may signify that IMD 16 is prepared to deliver electrical stimulation therapy to heart 12. Beat identification module 94 continues to receive the signal indicative of activity of heart 12 from sensing module 78 and, in response to completion of charging, applies the threshold amplitude value to the signal to identify a beat that exceeds the threshold amplitude value (130), e.g., a beat that falls within the first group of amplitude values. In accordance with the technique illustrated in FIG. 6, shock synchronization module 96 controls signal generator 76 to deliver an electrical shock to heart 12 synchronized to the identified beat to treat the cardiac arrhythmia of patient 14.

In some examples, processor 72 may perform additional tests to ensure that the first group of amplitude values is representative of authentic physiological activity of patient 14 and, consequently, that electrical stimulation therapy is accurately delivered in response to authentic physiological activity. As an example, beat analysis module 92 may analyze the plurality of beats during a particular amount of time, determine whether the first group of amplitude values includes an appropriate number of amplitude values relative to the particular amount of time, and synchronize delivery of the shock to the identified beat only if the first group of amplitude values includes an appropriate number of amplitude values.

For example, heart 12 of patient 14 may be expected to beat with a frequency falling within a particular range of frequencies, i.e., patient 14 may be expected to have a heart rate falling within a particular range of values. Beat analysis module 92 may calculate the amount of beats that would be expected for patient 14 within the particular amount of time based on the expected heart rate of patient 14 and subsequently determine whether or not the amount of amplitude values falling within the first group of amplitude values is equal to or substantially equal to the amount of beats that would be expected for patient 14 during that particular amount of time. If the amount of amplitude values falling within the first group of amplitude values is equal to or substantially equal to the amount of beats that would be expected, shock synchronization module 96 may synchronize delivery of the electrical stimulation shock to a subsequently detected beat falling within the first group of amplitude values.

Similarly, heart 12 of patient 14 may be expected to beat such that the time interval between respective beats of heart 12 is within a particular physiological range. Consequently, in some examples, beat analysis module 92 may determine whether or not the time interval between respective amplitude values falls within the particular physiological range in order to more accurately determine whether the beats are indicative of authentic physiological activity or other electrical activity, such as electrical noise. In some examples, if beat analysis module 92 determines that the amount of amplitude values or time interval between respective amplitude values does not fall within the acceptable physiological range, shock synchronization module 96 may not control signal generator 76 to synchronize delivery of a shock to a beat using the beat discriminator. In these examples, shock synchronization module 96 may control signal generator 76 to deliver a shock that is synchronized to any detected beat, e.g., any beat detected by sensing module 78, instead of using the beat discriminator to synchronize the shock.

In some examples, processor 72 may modify the threshold amplitude value that is the beat discriminator, e.g., that distinguishes between the first and second groups of amplitude values, until the first group of amplitude values includes an appropriate number of amplitude values relative to the amount of time over which processor 72 analyzes the amplitude values, or amplitude values with appropriate time intervals therebetween. For example, if processor 72 determines that the amount of amplitude values falling within the first group of amplitude values is greater than the amount of beats that would be expected, processor 72 may increase the threshold amplitude value that is the beat discriminator, which may result in fewer amplitude values falling within the first group of amplitude values. Similarly, if processor 72 determines that the amount of amplitude values falling within the first group of amplitude values is less than the amount of beats that would be expected, processor 72 may decrease the threshold amplitude value that is the beat discriminator, which may result in more amplitude values falling within the first group of amplitude values.

Although FIG. 8 is described with respect to beat analysis module 92 determining a beat discriminator, in other examples, beat analysis module 92 may not determine a beat discriminator, e.g., may be unable to determine a beat discriminator. For example, beat analysis module 92 may be unable to identify first and second groups of amplitude values in which each of the amplitude values of the first group exceeds each of the amplitude values of the second group of amplitude values by a predetermined value. That is, beat analysis module 92 may not identify a difference of at least the predetermined value between two adjacent amplitude values in a magnitude ordering. In examples in which beat analysis module 92 does not determine a beat discriminator, shock synchronization module 96 may control signal generator 76 to deliver a shock that is synchronized to any detected beat, e.g., any beat detected by sensing module 78.

Figure 9:
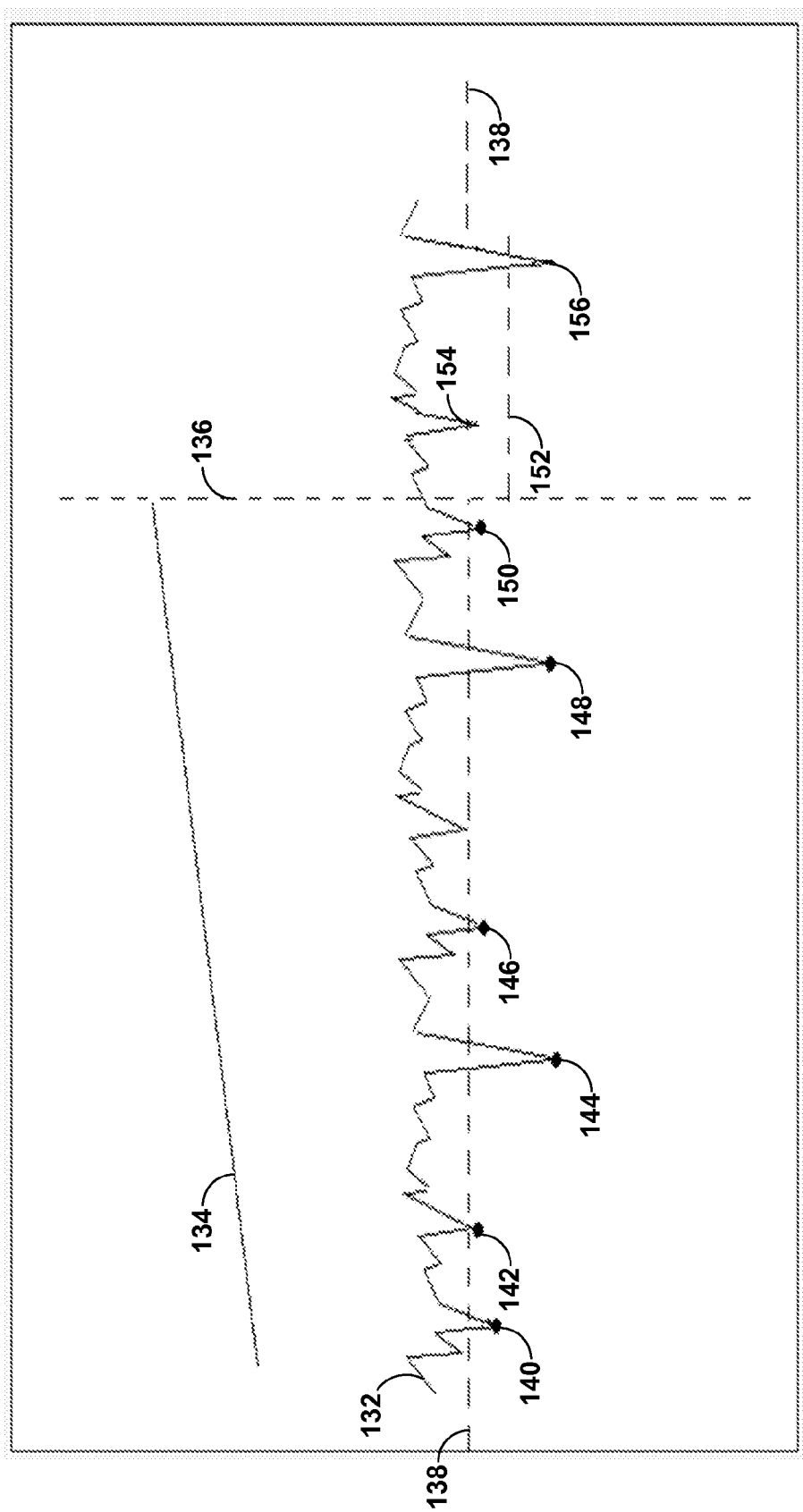
FIG. 9 is a graphical illustration representing determining a beat discriminator and identifying a beat for synchronization of electrical stimulation using the beat discriminator.

FIG. 9 is a graphical representation illustrating transitioning from analyzing electrical signal 132 using a first threshold amplitude value to analyzing electrical signal 132 using a second threshold amplitude value, and identifying a beat for synchronization of a shock by applying the second threshold amplitude value to a signal indicative of suspected cardiac arrhythmia of patient 14 after charging of one or more components of IMD 16.

FIG. 9 illustrates electrical signal 132 sensed by sensing module 78 and indicative of electrical activity of heart 12 of patient 14. In the example illustrated in FIG. 9, IMD 16 has determined based on electrical signal 132 that patient 12 is experiencing cardiac arrhythmia. As discussed previously, upon detection of cardiac arrhythmia, processor 72 may initiate charging of one or more components of signal generator 76. In FIG. 9, charge progression indicator 134 indicates the progression of charging until charging is complete, which is indicated by charge completion indicator 136.

As discussed previously, processor 72 detects beats in electrical signal 132 and determines that patient 14 is experiencing cardiac arrhythmia based on analyzing the beats, e.g., based on the frequency of the beats over time. As illustrated in FIG. 9, before completion of charging (as indicated by charge completion indicator 136), processor 72 identifies beats using a first amplitude threshold value 138. Consequently, before completion of charging, processor 72 identifies six beats 140, 142, 144, 146, 148, and 150 by applying the first amplitude threshold value 138 to the electrical signal 132.

As illustrated in FIG. 9, beats 140, 142, 144, 146, 148, and 150 are defined by varying amplitude values. For example, beats 144 and 148 are defined by amplitude values substantially greater than beats 140, 142, 146, and 150. In accordance with the technique illustrated in FIG. 8, processor 72 analyzes the amplitude values of beats 140, 142, 144, 146, 148, and 150. (For purposes of description, beats defined by greater amplitude values refer to beats defined by greater magnitudes of depolarization, e.g., greater changes in electrical signal 132.) Because beats 144 and 148 are defined by substantially greater amplitude values, processor 72 may determine that beats 144 and 148 comprise a first group of amplitude values. Similarly, because beats 140, 142, 146, and 150 are defined by substantially smaller amplitude values, processor 72 may determine that beats 140, 142, 146, and 150 comprise a second group of amplitude values. In some examples, beats 144 and 148 may be indicative of authentic ventricular depolarizations while beats 140, 142, 146, and 150 may be indicative of other electrical activity, e.g., electrical noise, sensed by IMD 16.

Based on determining that beats 144 and 148 comprise a first group of amplitude values and beats 140, 142, 146, and 150 comprise a second group of amplitude values, processor 72 may calculate or determine a second threshold amplitude value 152 that can distinguish between amplitude values falling within the first group and amplitude values falling within the second group.

Upon completion of charging (as indicated by charge completion indicator 136) and determination of second threshold amplitude value 152, processor 72 may identify only beats falling within the first group of amplitude values for synchronization of electrical stimulation shock to treat the cardiac arrhythmia. For example, in the example illustrated in FIG. 9, beat 154 is defined by an amplitude value falling within the second group of amplitude values, e.g., falling above second threshold amplitude value 152 in FIG. 9. Consequently, processor 72 may not control signal generator 76 to deliver a shock synchronized with beat 154. In contrast, beat 156 is defined by an amplitude value falling within the first group of amplitude values, e.g., falling below the second threshold amplitude value 152 in FIG. 9. Consequently, processor 72 may control signal generator 76 to deliver a shock synchronized with beat 156. In this way, IMD 16 can accurately synchronize delivery of electrical stimulation to treat a cardiac arrhythmia with authentic cardiac events and activity.

In some examples, a component of system 10 may store one or more parameters used by processor 72 to analyze electrical signal 132 and to synchronize a shock with an identified beat. For example, system 10 may store parameters such as first amplitude threshold value 138 and second threshold amplitude value 152, correlated with the portion of electrical signal 132 to which first amplitude threshold value 138 and second threshold amplitude value 152 apply. In some examples, system 10 may store the parameters and corresponding electrical signal segments in a memory of system 10, such as memory 74 of IMD 16 or a memory of programmer 24, such that a user or a component of IMD 16 may retrieve and review the parameters and corresponding electrical signal segments at a later time.

In some examples, a component of system 10, such as programmer 24, may display a portion of electrical signal 132 and the corresponding parameters to a user. For example, programmer 24 may display the graphical representation shown in FIG. 9 via a display of programmer 24 to a user such that the user can view the analysis performed by processor 72 "in action" for a particular segment of electrical signal 132, e.g., a segment of electrical signal 132 that is representative of a suspected cardiac arrhythmia. In some examples, the display may be interactive, and the user, e.g., a clinician, may modify one or more parameters, such as one or more threshold values or a beat discriminator determined by processor 72, by providing feedback to the interactive display. For example, the display may include a touch screen, and a user may use a finger or a stylus to modify first amplitude threshold value 138 and/or second amplitude threshold value 152, e.g., by moving the lines representing first amplitude threshold value 138 and second threshold amplitude value 152 up or down on the display, to more effectively treat the suspected cardiac arrhythmia of patient 14.

Figure 10:
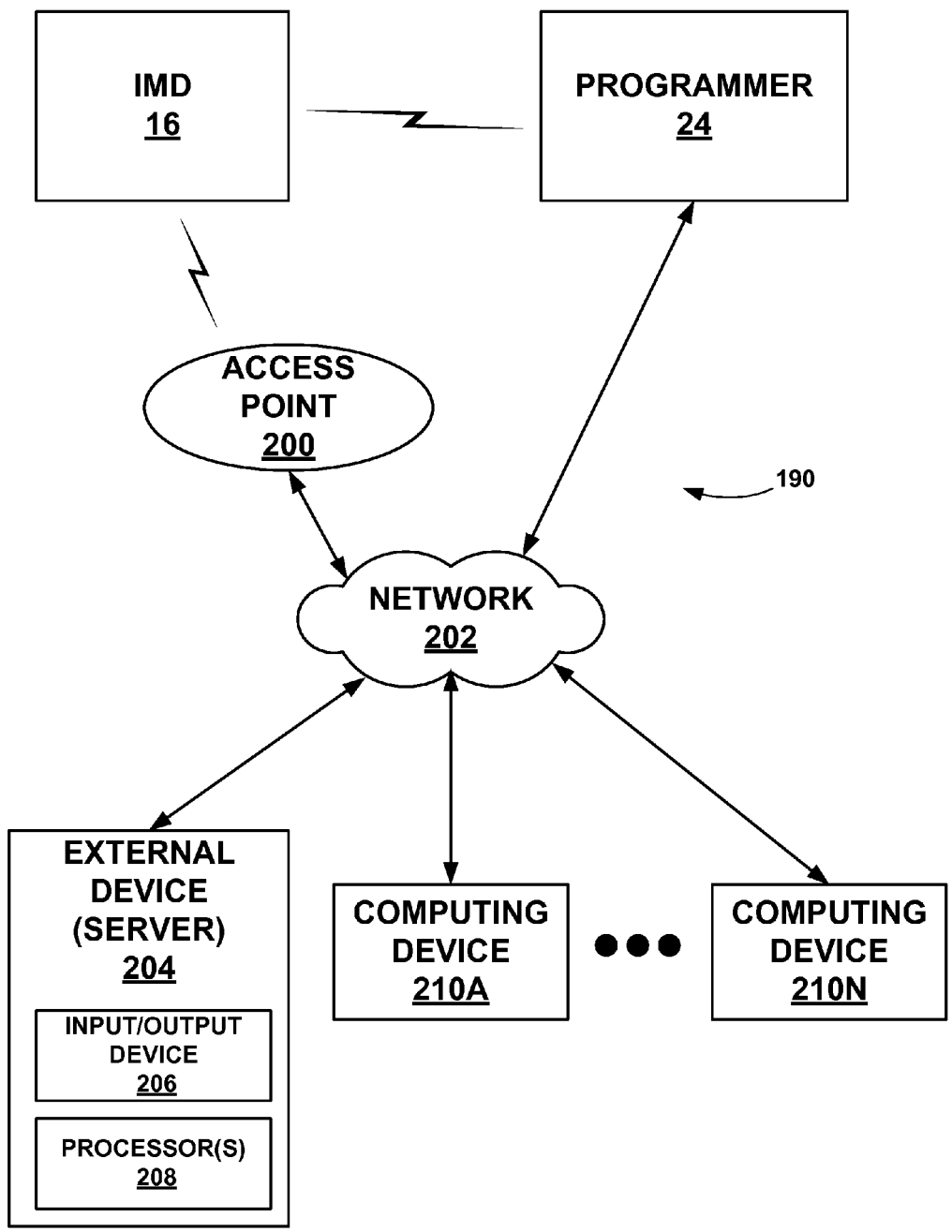
FIG. 10 is a block diagram illustrating an example system that includes an external device, such as a server, and one or more computing devices that are coupled to the IMD and programmer shown in FIG. 1 via a network.

FIG. 10 is a block diagram illustrating an example system 190 that includes an external device, such as a server 204, and one or more computing devices 210A-210N, that are coupled to the IMD 16 and programmer 24 shown in FIG. 1 via a network 202. In this example, IMD 16 may use its telemetry module 88 to communicate with programmer 24 via a first wireless connection, and to communicate with an access point 200 via a second wireless connection. In the example of FIG. 10, access point 200, programmer 24, server 204, and computing devices 210A-210N are interconnected, and able to communicate with each other, through network 202. In some cases, one or more of access point 200, programmer 24, server 204, and computing devices 210A-210N may be coupled to network 202 through one or more wireless connections. IMD 16, programmer 24, server 204, and computing devices 210A-210N may each comprise one or more processors, such as one or more microprocessors, DSPs, ASICs, FPGAs, programmable logic circuitry, or the like, that may perform various functions and operations, such as those described herein. For example, as illustrated in FIG. 10, server 204 may comprise one or more processors 208 and an input/output device 206, which need not be co-located.

Server 204 may, for example, practice the methods described herein for synchronizing a shock to an identified beat using a beat discriminator. Server 204 may implement any or all of the modules illustrated in FIGS. 4 and 5 and perform any or all of the techniques illustrated in FIGS. 6-8. Furthermore, in some examples, server 204 may provide a database for storing signal data, which may be provided by server 204 as one example, or by programmer 24 as another.

Access point 200 may comprise a device that connects to network 202 via any of a variety of connections, such as telephone dial-up, digital subscriber line (DSL), or cable modem connections. In other embodiments, access point 200 may be coupled to network 202 through different forms of connections, including wired or wireless connections. In some embodiments, access point 200 may be co-located with patient 14 and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16. In some embodiments, server 204 or one or more of the computing devices 210A-210N may perform any of the various functions or operations described herein.

Network 202 may comprise a local area network, wide area network, or global network, such as the Internet. In some cases, programmer 24 or server 204 may assemble data related to synchronization of electrical stimulation therapy with an identified beat based on a beat discriminator, in web pages or other documents for viewing by patients and/or trained professionals, such as clinicians, via viewing terminals associated with computing devices 210A-210N. System 190 may be implemented, in some aspects, with general network technology and functionality similar to that provided by the Medtronic CareLink® Network developed by Medtronic, Inc., of Minneapolis, Minn.

Although the disclosure is described with respect to cardiac stimulation therapy, such techniques may be applicable to other therapies in which lead integrity is important, such as, e.g., spinal cord stimulation, deep brain stimulation, pelvic floor stimulation, gastric stimulation, occipital stimulation, functional electrical stimulation, and the like. In such therapies, the techniques described in this disclosure may be applied to detect possible lead-related conditions.

The techniques described in this disclosure, including those attributed to IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A method comprising:
    receiving a signal indicative of activity of a heart of a patient;
    detecting beats within the signal;
    detecting a suspected cardiac arrhythmia based on a plurality of the detected beats;
    initiating charging of at least one component of an implantable device configured to deliver a shock to the heart of the patient to treat the cardiac arrhythmia in response to detecting the suspected cardiac arrhythmia;
    analyzing the plurality of beats subsequent to the detection of the suspected cardiac arrhythmia to determine a beat discriminator;
    in response to completion of the charging, applying the beat discriminator to the signal to identify a beat subsequent to the completion of the charging; and
    synchronizing delivery of the shock to the identified beat.

2. The method of claim 1, further comprising resetting the beat discriminator subsequent to synchronizing delivery of the shock to the identified beat.

3. The method of claim 1, wherein analyzing the plurality of the beats subsequent to the detection of the suspected cardiac arrhythmia to determine a beat discriminator comprises analyzing the plurality of the beats during the charging of the at least one component to determine the beat discriminator.

4. A method, comprising:
    receiving a signal indicative of activity of a heart of a patient;
    detecting beats within the signal;
    detecting a suspected cardiac arrhythmia based on a plurality of the detected beats;
    initiating charging of at least one component of an implantable device configured to deliver a shock to the heart of the patient to treat the cardiac arrhythmia in response to detecting the suspected cardiac arrhythmia;
    analyzing the plurality of beats subsequent to the detection of the suspected cardiac arrhythmia to determine a beat discriminator;
    in response to completion of the charging, applying the beat discriminator to the signal to identify a beat subsequent to the completion of the charging; and
    synchronizing delivery of the shock to the identified beat,
    wherein analyzing the plurality of beats subsequent to the detection of the suspected cardiac arrhythmia to determine a beat discriminator comprises:
        analyzing a plurality of amplitude values, wherein each of the plurality of amplitude values is associated with a respective one of the plurality of beats; and
        determining that the plurality of amplitude values comprises a first group of amplitude values and a second group of amplitude values based on analyzing the plurality of amplitude values,
    wherein applying the beat discriminator to the signal to identify a beat comprises identifying a beat having an amplitude value falling within the first group of amplitude values.

5. The method of claim 4, wherein the first group of amplitude values at least partially represents a group of physiological cardiac events of the patient and wherein the second group of amplitude values at least partially represents electrical noise.

6. The method of claim 4, further comprising determining a threshold amplitude value greater than each of the amplitude values in the second group of amplitude values, wherein identifying a beat having an amplitude value falling within the first group of amplitude values comprises identifying a beat based on applying the threshold amplitude value to the signal subsequent to completion of the charging.

7. The method of claim 4, wherein each of the amplitude values of the first group of amplitude values exceeds each of the amplitude values of the second group of amplitude values by at least a predetermined value.

8. The method of claim 7, wherein the predetermined value is approximately 0.5 milliVolts (mV).

9. The method of claim 7, wherein analyzing the plurality of beats occurs during a particular amount of time, and wherein the method further comprises determining that the first group of amplitude values includes an appropriate number of amplitude values relative to the particular amount of time, and wherein synchronizing delivery of the shock to the identified beat comprises synchronizing delivery of the shock to the identified beat if the first group of amplitude values includes an appropriate number of amplitude values relative to the particular amount of time.

10. The method of claim 9,
further comprising determining a threshold amplitude value greater than each of the amplitude values in the second group of amplitude values, wherein identifying a beat having an amplitude value falling within the first group of amplitude values comprises identifying a beat based on applying the threshold amplitude value to the signal subsequent to completion of the charging,
wherein the method further comprises modifying the threshold amplitude value until the first group of amplitude values includes the appropriate number of amplitude values.

11. The method of claim 1, wherein receiving a signal indicative of activity of a heart of a patient comprises receiving a plurality of signals indicative of activity of the heart of the patient, and wherein detecting beats within the signal comprises detecting beats within each of the plurality of signals and determining a number of beats within each of the plurality of signals, wherein the method further comprises:
comparing the number of beats within each of the plurality of signals to one another; and
selecting one of the plurality of signals based on the comparison.

12. The method of claim 1, further comprising:
displaying, via a display, a graphical representation of the signal and the beat discriminator; and
receiving feedback, via the display, wherein the feedback is related to the beat discriminator.

13. A system comprising:
a signal generator configured to deliver a shock to a heart of a patient to treat a cardiac arrhythmia of the patient;
a sensing module configured to sense a signal indicative of activity of the heart of the patient; and
a processor comprising:
a signal receiving module configured to receive the signal,
a beat detection module configured to detect beats within the signal,
an arrhythmia detection module configured to detect a suspected cardiac arrhythmia based on a plurality of the detected beats,
a charge initiating module configured to initiate charging of at least one component of the signal generator in response to detecting the suspected cardiac arrhythmia,
a beat analysis module configured to analyze the plurality of the beats subsequent to the detection of the suspected cardiac arrhythmia to determine a beat discriminator,
a beat identification module configured to, in response to completion of the charging of the signal generator, apply the beat discriminator to the signal to identify a beat subsequent to the completion of the charging of the signal generator, and
a shock synchronization module configured to control the signal generator to synchronize delivery of the shock to the identified beat.

14. The system of claim 13, wherein the beat analysis module analyzes the plurality of beats during the charging of the at least one component to determine the beat discriminator.

15. A system, comprising:
a signal generator configured to deliver a shock to a heart of a patient to treat a cardiac arrhythmia of the patient;
a sensing module configured to sense a signal indicative of activity of the heart of the patient; and
a processor comprising:
a signal receiving module configured to receive the signal,
a beat detection module configured to detect beats within the signal,
an arrhythmia detection module configured to detect a suspected cardiac arrhythmia based on a plurality of the detected beats,
a charge initiating module configured to initiate charging of at least one component of the signal generator in response to detecting the suspected cardiac arrhythmia,
a beat analysis module configured to analyze the plurality of the beats subsequent to the detection of the suspected cardiac arrhythmia to determine a beat discriminator,
a beat identification module configured to, in response to completion of the charging of the signal generator, apply the beat discriminator to the signal to identify a beat subsequent to the completion of the charging of the signal generator, and
a shock synchronization module configured to control the signal generator to synchronize delivery of the shock to the identified beat,
wherein the beat analysis module analyzes the plurality of beats by analyzing a plurality of amplitude values, wherein each of the plurality of amplitude values is associated with a respective one of the plurality of beats, and determines that the plurality of amplitude values comprises a first group of amplitude values and a second group of amplitude values based on analyzing the plurality of amplitude values, and wherein the beat identification module applies the beat discriminator to the signal to identify a beat by identifying a beat having an amplitude value falling within the first group of amplitude values.

16. The system of claim 15, wherein the first group of amplitude values at least partially represents a group of physiological cardiac events of the patient and wherein the second group of amplitude values at least partially represents electrical noise.

17. The system of claim 15, wherein the processor is configured to determine a threshold amplitude value greater than each of the amplitude values in the second group of amplitude values and wherein the beat identification module applies the beat discriminator to the signal to identify a beat subsequent to the completion of the charging by identifying a beat based on applying the threshold amplitude value to the signal subsequent to completion of the charging.

18. The system of claim 15, wherein each of the amplitude values of the first group of amplitude values exceeds each of the amplitude values of the second group of amplitude values by at least a predetermined value.

19. A system comprising:
means for receiving a signal indicative of activity of a heart of a patient;
means for detecting beats within the signal;

means for detecting a suspected cardiac arrhythmia based on a plurality of the detected beats;
means for initiating charging of at least one component of an implantable device configured to deliver a shock to the heart of the patient to treat the cardiac arrhythmia in response to detecting the suspected cardiac arrhythmia;
means for analyzing the plurality of the beats subsequent to the detection of the suspected cardiac arrhythmia to determine a beat discriminator;
means for, in response to completion of the charging, applying the beat discriminator to the signal to identify a beat subsequent to the completion of the charging; and
means for synchronizing delivery of the shock to the identified beat.

20. A system, comprising:
means for receiving a signal indicative of activity of a heart of a patient;
means for detecting beats within the signal;
means for detecting a suspected cardiac arrhythmia based on a plurality of the detected beats;
means for initiating charging of at least one component of an implantable device configured to deliver a shock to the heart of the patient to treat the cardiac arrhythmia in response to detecting the suspected cardiac arrhythmia;
means for analyzing the plurality of the beats subsequent to the detection of the suspected cardiac arrhythmia to determine a beat discriminator;
means for, in response to completion of the charging, applying the beat discriminator to the signal to identify a beat subsequent to the completion of the charging; and
means for synchronizing delivery of the shock to the identified beat,
wherein the means for analyzing a plurality of the beats analyzes the plurality of beats by analyzing a plurality of amplitude values, wherein each of the plurality of amplitude values is associated with a respective one of the plurality of beats, and determines that the plurality of amplitude values comprises a first group of amplitude values and a second group of amplitude values based on analyzing the plurality of amplitude values, and wherein the means for applying the beat discriminator applies the beat discriminator to the signal to identify a beat by identifying a beat having an amplitude value falling within the first group of amplitude values.

21. The system of claim 20, wherein the first group of amplitude values at least partially represents a group of physiological cardiac events of the patient and wherein the second group of amplitude values at least partially represents electrical noise.

22. A non-transitory computer-readable storage medium comprising instructions that cause a processor to:
receive a signal indicative of activity of a heart of a patient;
detect beats within the signal;
detect a suspected cardiac arrhythmia based on a plurality of the detected beats;
initiate charging of at least one component of an implantable device configured to deliver a shock to the heart of the patient to treat the cardiac arrhythmia in response to detecting the suspected cardiac arrhythmia;
analyze the plurality of the beats subsequent to the detection of the suspected cardiac arrhythmia to determine a beat discriminator;
in response to completion of the charging, apply the beat discriminator to the signal to identify a beat subsequent to the completion of the charging; and
synchronize delivery of the shock to the identified beat.

23. A non-transitory computer-readable storage medium, comprising:
receive a signal indicative of activity of a heart of a patient;
detect beats within the signal;
detect a suspected cardiac arrhythmia based on a plurality of the detected beats;
initiate charging of at least one component of an implantable device configured to deliver a shock to the heart of the patient to treat the cardiac arrhythmia in response to detecting the suspected cardiac arrhythmia;
analyze the plurality of the beats subsequent to the detection of the suspected cardiac arrhythmia to determine a beat discriminator;
in response to completion of the charging, apply the beat discriminator to the signal to identify a beat subsequent to the completion of the charging; and
synchronize delivery of the shock to the identified beat,
wherein the instructions cause the processor to analyze the plurality of beats subsequent to the detection of the suspected cardiac arrhythmia to determine a beat discriminator analyzing a plurality of amplitude values, wherein each of the plurality of amplitude values is associated with a respective one of the plurality of beats, and determine that the plurality of amplitude values comprises a first group of amplitude values and a second group of amplitude values based on analyzing the plurality of amplitude values, wherein the instructions cause the processor to apply the beat discriminator to the signal to identify a beat by identifying a beat having an amplitude value falling within the first group of amplitude values.

24. The computer-readable storage medium of claim 23, wherein the first group of amplitude values at least partially represents a group of physiological cardiac events of the patient and wherein the second group of amplitude values at least partially represents electrical noise.

* * * * *